US008484270B2

(12) United States Patent
Kurtz et al.

(10) Patent No.: US 8,484,270 B2
(45) Date of Patent: Jul. 9, 2013

(54) SYSTEM AND METHOD FOR ADAPTIVE STIMULUS-RESPONSE SIGNAL FILTERING

(75) Inventors: Isaac Kurtz, Toronto (CA); Aaron Steinman, Etobicoke (CA); Yuri Sokolov, Mississauga (CA)

(73) Assignee: Vivosonic Inc., Etobicoke, ON. (CA)

( * ) Notice: Subject to any disclaimer, the term of this patent is extended or adjusted under 35 U.S.C. 154(b) by 1130 days.

(21) Appl. No.: 12/138,271

(22) Filed: Jun. 12, 2008

(65) Prior Publication Data

US 2009/0149148 A1 Jun. 11, 2009

Related U.S. Application Data

(60) Provisional application No. 60/943,387, filed on Jun. 12, 2007.

(51) Int. Cl.
*G06F 17/10* (2006.01)
(52) U.S. Cl.
USPC .......................................................... 708/300
(58) Field of Classification Search
None
See application file for complete search history.

(56) References Cited

U.S. PATENT DOCUMENTS

| 5,697,379 | A | 12/1997 | Neely et al. | |
| 5,792,073 | A | 8/1998 | Keefe | |
| 6,009,448 | A * | 12/1999 | Jong et al. | 708/322 |
| 2008/0109041 | A1 * | 5/2008 | de Voir | 607/7 |

OTHER PUBLICATIONS

Steinman et al.: "A More Reliable Method to Verify Auditory Evoked Potential Repeatability"; Presented at the annual meeting of the American Auditory Society; Mar. 6-8, 2008, Scottsdale, AZ, U.S.A.; http://www.vivosonic.com/pdf/more-reliable-method-to-verity-evoked-potential-repeatability.pdf; Accessed Sep. 10, 2008.
Sokolov,Y.; "Auditory Evoked Potentials; Signals, Noises & Clear Recording Through New Technologies—In-situ Amplifications, Wireless Communications & Kalman Filtering"; NCHAM Workshop, Apr. 21-22, 2005, Albuquerque, NM, U.S.A.; http://www.vivosonic.com/pdf/auditory-evoked-potentials-new-technologies-2005; Accessed Sep. 10, 2008.
Qin et al.: "The Study About the Reduction of the Stimulus Artifact Using PSR Filter"; Proceedings of the 2005 IEEE Engineering in Medicine and Biology 27th Annual Conference, pp. 1185-1188; Shanghai, China, Sep. 1-4, 2005.
International Searching Authority, International Search Report, Sep. 25, 2008, PCT/CA2008/00142.
International Searching Authority, The Written Opinion of the International Searching Authority, Sep. 25, 2008.

* cited by examiner

*Primary Examiner* — David H Malzahn
(74) *Attorney, Agent, or Firm* — Borden Ladner Gervais LLP; Neil Henderson

(57) ABSTRACT

A system and method for filtering a signal comprising: receiving a signal of interest; receiving a signal indicating that a stimulus has been applied; receiving the synchronized stimulus signal and signal of interest; recursively selecting a portion of the signal of interest associated with a stimulus being applied and assign the selected portion of the signal of interest to one of the plurality of buffers; combining all responses in each of said plurality of buffers; transforming the combination of all responses in each buffer to a transform space; comparing the transform components of the buffers to determine a scaling factor; applying the scaling factor to the spectral components of the buffers; performing an inverse transform on the result of combining the buffers to return to the time domain to produce a filtered signal, and outputting the filtered signal received from the processor.

18 Claims, 5 Drawing Sheets

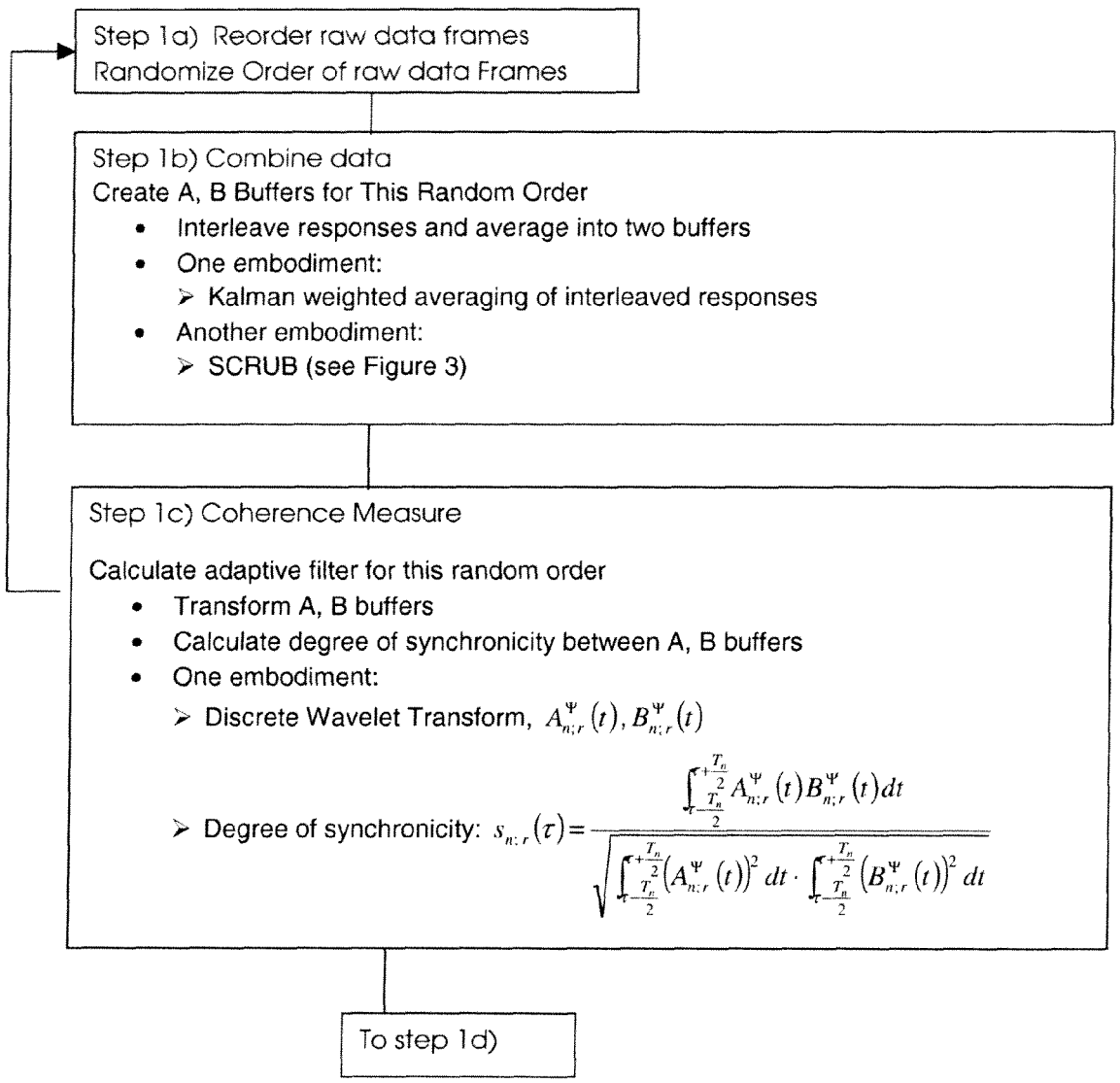
FIG. 1A SNR Optimized Adaptive Processor (SOAP)

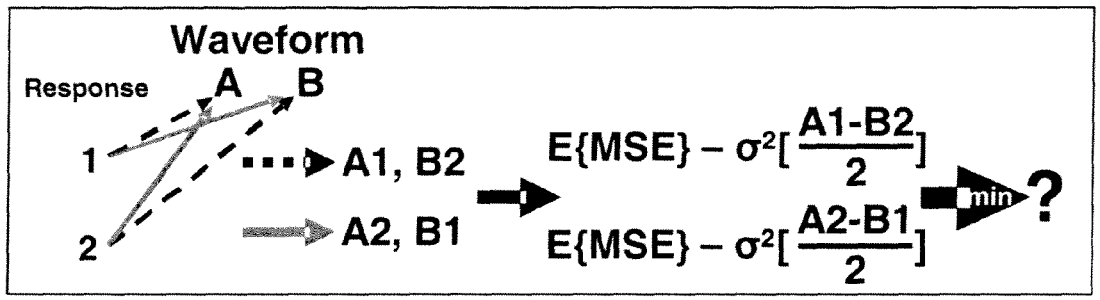

- Collect next 2 raw data responses: Response1 and Response2
- Preprocess signal with a preferred filter
- Create two buffer pair candidates:

BufferingCandidate1) Response1 weighted and averaged to buffer A, Response2 to buffer B BufferingCandidate2) Response1 weighted and averaged to buffer B, Response2 to buffer A

- One Embodiment:
    - Kalman weighted averaging to combine responses in buffer candidates Decision: Which Buffering Candidate to Use?

- Apply decision algorithm to both candidates
- One Embodiment:
    - Compare the expected mean square error (the resultant error covariance generated by the Kalman filter) with the variance of the error for each buffering candidate, i.e. variance of (A-B)/2
    - The buffering candidate that minimizes the differences between the errors will be selected, since the variance of (A-B)/2 for that buffering candidate most closely represents the expected error Figure 2 Selection of Coefficient of Regression for Uniform Buffering (SCRUB)

SYSTEM AND METHOD FOR ADAPTIVE STIMULUS-RESPONSE SIGNAL FILTERING

PRIORITY CLAIM

This application claims the priority of U.S. Provisional Application No. 60/943,387 filed on Jun. 12, 2007, the entire content of which is hereby incorporated by reference.

TECHNICAL FIELD

This application relates to systems and methods for adaptive filtering of a signal generated in response to a stimulus (a stimulus-response signal). In particular, the application relates to systems and methods for adaptive stimulus-response signal filtering when there is a low signal to noise ratio such as in electrophysiological evoked responses.

BACKGROUND

The are many situations in which is necessary to extract a signal of interest from a noisy received signal. This task becomes harder in a situation in which the received signal has a low signal to noise ratio (SNR). In some cases, the signal of interest is generated in response to a stimulus. An example of such a case relates to the measurement of evoked responses. Electrophysiological evoked responses to a variety of stimuli are known to contain valuable clinical and scientific information in the assessment of the sensorineural systems of humans and animals. Evoked responses (ER), such as, for example, auditory evoked potentials, somatosensory evoked potentials, visual evoked potentials or otoacoustic emissions, are signals that are often 10-1000 times smaller than the noise that is typically recorded by signal transducers (such as electrodes or microphones) at the time of recording the ER. In many cases, the ER waveform and its clinically relevant features are only detectable after averaging thousands of responses to individual stimuli.

The noise that is recorded by the signal transducers may be from various sources, including, for example, noise generated by muscular activity (for example, EMS noise) during an evoked response (ER) test and may include other types of electrical noise from lighting, other instruments and the like. Because the noise is generally many times greater than the ER signal, the noise tends to mask the ER signal. One challenge of clinical ER measurement is determining whether specific features of an ER waveform represent true electrophysiological responses or if they are noise. A special application of ER detection is the detection of the auditory brainstem response (ABR) and auditory steady state responses with applications to infant hearing screening and to the determination of auditory thresholds, which may be used in the customized fitting of hearing aids. Detection of evoked responses may be performed manually by a clinician trained to recognize the ER waveform of interest or automatically with computer-based automated detection. In either case, detection is severely impaired by the presence of noise.

Automated response detection techniques include statistical methods and template matching methods. $F_{SP}$ is one statistical approach which uses a variance ratio to compare the signal estimate to the estimated averaged background noise (M. Don et al. "Objective Detection of Averaged Auditory Brainstem Responses" *Scand Audiol.* 1984; 13(4):219-28). Template matching methods detect the presence of a response by comparing the test waveform to another waveform previously learned by the system or acquired under similar conditions. There are also statistical techniques that use a priori knowledge of the waveform from a previously learned template to optimize the power of the statistical test (U.S. Pat. No. 6,196,917, Issue date: Mar. 6, 2001, Inventors: Yvonne S. Sininger, Martyn Hyde, Manuel Don).

Several techniques used to minimize noise in the recorded response to auditory stimuli are summarized in "M. Don and C. Elberling, Evaluating Residual Background Noise in Human Auditory Brain-Stem Responses, J. Acoust. Soc. Am. 96 (5), (1994)". These techniques include signal averaging and weighted signal averaging, signal filtering, artifact rejection, and various techniques designed to relax or sedate the subject.

Signal averaging involves stimulating the patient with multiple stimuli, obtaining multiple time-based signal streams synchronized to the application of each of the multiple stimuli, and averaging the synchronized signal streams. Limitations of this traditional averaging method in evoked potential acquisition have long been recognized. The problem arises primarily from the poor signal to noise ratio (SNR) and the fact that the number of averages required, typically increases in inverse proportion to the square of the SNR. In a typical case of 10 microVolts of noise, to obtain a measurement of threshold-level auditory brainstem response of 100 nanoVolts with a modest SNR of 2:1 would require, on average, averaging responses to 40,000 stimuli. Under the constraint that the stimulus is not repeated until the response to the previous stimulus is received, there is an upper limit on the stimulus repetition rate. Furthermore, evoked responses may degrade when the stimulus repetition rate is too fast. In practical ABR screening systems, the stimulus repetition rate is limited to approximately 40 stimuli per second. More than 16 minutes would therefore be required to achieve a modest SNR of 2:1 in this example.

Artifact rejection (AR) can be used to eliminate epochs that are most contaminated with noise, by excluding those epochs for which the noise exceeds a preset threshold. Weighted averaging (WA) further improves SNR by weighting each epoch in inverse proportion to its noise content (see for example J. Sanchez and D. Gans, American Journal of Audiology Vol. 15 154-163, "Effects of Artifact Rejection and Bayesian Weighting on the Auditory Brainstem Response During Quiet and Active Behavioral Conditions"). Weighted averaging may be designed to optimize the SNR in the response by selecting weights according to Kalman Filter theory (J. eski, "New concept of signal averaging in time domain", Annual International Conference of the IEEE Engineering in Medicine and Biology Society, Vol. 13:1, 1991, 367-368). This technique presumes an estimate of the error variance in the raw data. A variety of techniques for estimating error variance have been suggested in the prior art (see Jacek M. eski, "Robust Weighted Averaging", IEEE Transactions on Biomedical Engineering, V49:8, August 2002 and Li, Sokolov, Kunov, U.S. Pat. No. 7,286,983, "Signal and Method for Processing Low Signal-to-noise Ratio Signals") but the inability to directly measure the error variance remains a drawback of the technique.

An important drawback of artifact rejection and weighted averaging is that when the noise is constantly present throughout the test, such as would be the case with an awake baby being tested for ABR, they are of limited use because equal amounts of signal and noise are removed.

Bandpass filtering may somewhat improve signal-to-noise ratio for detecting the low frequency components of some ERs, but is generally not helpful in the detection of the ABR, for example, since most of the ABR spectrum is contained within the same bandwidth as the EMG noise spectrum. For this reason, drug-induced sedation is usually required for ABR testing in babies and children from 6 months to 4 or 5 years of age (James Hall, *New Handbook of Auditory Evoked Responses*, Pearson Education Inc., 2007, p. 306). As will be understood the use of drug-induced sedation is preferably avoided.

Systems designed to detect and estimate ER signals, typically also estimate the noise (for example, the noise magnitude or the noise spectrum) contained in the estimated ER signal and the signal-to-noise ratio of the estimated ER signal. The estimated noise magnitude and signal-to-noise ratio may be conveyed to the user as an indication of confidence in the result. These estimates may be used in the calculation of test statistics to estimate the probability of the presence or absence of a response. The noise spectrum may be used to adaptively apply a filter that is optimized to eliminate the noise from the signal estimate.

One way to estimate the noise magnitude, used in the $F_{SP}$ technique cited above (M. Don et al., 1984) is to measure the variability of the recorded potential in all responses at a fixed latency relative to the stimulus. This technique provides a robust estimate of the noise magnitude but does not provide an estimate of the noise spectrum.

An estimate of the noise spectrum may be obtained from the spectrum during the prestimulus period (used in, for example, U.S. Pat. No. 5,230,344 Inventors Ozdamar, Ozcan and Delgado, Rafael E.). This technique has the disadvantage that the spectrum during the prestimulus period may not be identical to the noise spectrum that contaminates the ER signal and it may contain spectral components due to later latency responses.

One technique used to overcome this disadvantage is to transform the raw signal using a Discrete Fourier Transform (J. Fridman et al., Application of Digital Filtering and Automatic Peak Detection to Brainstem Auditory Evoked Potential, Electroencephalogy and Clinical Neurophysiology, 1982) and examining the phase coherence of each spectral component. Component that are more coherent are assumed to have a higher SNR than components that are less coherent. The disadvantage of this technique is that Fourier Transforms are not well suited to analyzing ER signals which, in general, are transient signals in which the magnitude and phase of individual components may vary within the analysis window.

This disadvantage was overcome with the introduction of the Complex Wavelet Transform (Arnaud Jacquin Elvir Causevic Roy John Jelena Kovacevic, "ADAPTIVE COMPLEX WAVELET-BASED FILTERING OF EEG FOR EXTRACTION OF EVOKED POTENTIAL", ICASSP 2005) in which the phase coherence of each spectral component is used to assess that component's SNR. If the noise spectrum is variable (non-white) and differs significantly from the signal spectrum, eliminating or reducing incoherent components and applying the inverse transform to the data has been shown to improve signal to noise ratio better than conventional averaging. One disadvantage of this technique is that the phase coherence estimate is itself unreliable for low signal-to-noise ratio signals and must be based on a large number of averages to be reliable. Furthermore the repeated application of the complex wavelet transform is computationally far more complex than the Fourier Transform. Use of the relatively simpler Discrete Wavelet Transform could not be applied, since the transform components of the DWT are real values and do have a phase component.

One solution to this problem, presented by Causevic et al. (U.S. Pat. No. 7,333,619 "Fast wavelet estimation of weak bio-signals using novel algorithms for generating multiple additional data frames") is to use a variable coherence threshold for the inclusion of discrete wavelet transform components in the signal. In this technique subaverages are created recursively in a binary tree structure (i.e. pairs of raw data frames are averaged and denoised to form a derived data frame, then pairs of those data frames are averaged and denoised to form the next level of data frames, etc.). For the purposes of this algorithm Causevic et al. defined coherence, not in terms of phase coherence which applies only to complex wavelet transforms as explained above, but rather in terms of the number of wavelet coefficients required to represent 99% of the signal. This approach has several apparent disadvantages recognized by Causevic et al. The signal being estimated must be coherent and smooth, when compared to the noise that corrupts it, i.e. it must be representable by relatively few wavelet coefficients because this is the basis of wavelet de-noising used by the authors. Secondly, the algorithm requires that all the frames of data be collected and stored prior to the application of the algorithm (i.e., for processing 512 frames, all of the 512 frames must be available in memory).

Another practice used to estimate the characteristics of the noise is to obtain multiple averages from independent sets of individual stimuli. The multiple averages may be collected sequentially or they may be obtained from interleaved data. Typically each response to each individual stimulus is assigned to one of two buffers designated Buffer A and Buffer B. Subsequent single-sweep responses are alternately assigned to a buffer, typically the odd-numbered responses in Buffer A and the even-numbered responses in Buffer B. The responses are combined with previous data in the assigned buffer using a conventional method such as for example averaging or weighted averaging. The spectrum and statistics of the waveform generated by subtracting the buffers (A−B in the typical case) then provides an estimate of the spectrum and statistics of the noise that contaminates the estimated ER signal. Alternatively the phase difference between the A and B spectra may be considered a measure of the phase coherence of each spectral component. The noise may be characterized as the variance of the (A−B)/2 buffer and SNR may be estimated as the variance ratio of the A+B to the A−B buffers. Furthermore, the coefficient of regression between buffers can be a measure of response repeatability and is related to the actual signal-to-noise ratio. The disadvantage of this method is that the estimate of A−B is unreliable and depends on the arbitrary assignment of raw data to buffers A and B. From a statistical perspective, the reliability of the estimate of the phase difference between A and B, will increase with the number of raw data frames used to generate A and B. The variance ratio used to estimate SNR, with the A−B variance in the denominator, is a poor estimator because degrees of freedom of this estimate is limited by relatively low number of cycles contained in the lowest frequency components in the estimate.

As such there is a need for improved systems and methods for processing and analysis of evoked responses.

SUMMARY

According to one aspect, there is provided a system for filtering a signal comprising: an input module for receiving a signal of interest; a stimulus input module for receiving a signal indicating that a stimulus has been applied; a plurality of memory buffers; and a processor configured to: receive the synchronized stimulus signal and signal of interest; recursively select a portion of the signal of interest associated with a stimulus being applied and assign the selected portion of the signal of interest to one of the plurality of buffers; combine all responses in each of said plurality of buffers; transform the combination of all responses in each buffer to a transform space; compare the transform components of the buffers to determine a scaling factor; apply the scaling factor to the spectral components of the buffers; and perform an inverse transform on the result of combining the buffers to return to the time domain to produce a filtered signal, and an output module configured to output the filtered signal received from the processor.

According to another aspect, there is provided a system for buffering a signal comprising: an input module for receiving a signal of interest; a stimulus input module for receiving a signal indicating that a stimulus has been applied; each received signal associated with a stimulus is assigned to a plurality of buffers comprising: sampling the signal of interest at a time corresponding to the associated stimulus to obtain a sample signal; and assigning the sampled signal to one of the plurality of buffers in a biased manner based on a comparative statistic related to measure of presence or the ER signal.

The filtering and buffering systems noted above may be advantageously be combined into a system to both filter and buffer a signal.

In a particular case of the buffering system, the comparative statistic is mean squared error and the assigning the sampled signal to one of the plurality of buffers in a biased manner comprises: first assigning a plurality of sampled signals to the plurality of buffers and calculating an error estimate between buffers; second assigning the plurality of sampled signals to the plurality of buffers in an order that is different from the first assigning and calculating a error estimate between buffers; and selecting the assignment that provides an error estimate that is closer to a target error estimate.

According to another aspect, there is provided a method for filtering a signal comprising: receiving a signal of interest; receiving a signal indicating that a stimulus has been applied; receiving the synchronized stimulus signal and signal of interest; recursively selecting a portion of the signal of interest associated with a stimulus being applied and assign the selected portion of the signal of interest to one of the plurality of buffers; combining all responses in each of said plurality of buffers; transforming the combination of all responses in each buffer to a transform space; comparing the transform components of the buffers to determine a scaling factor; applying the scaling factor to the spectral components of the buffers; performing an inverse transform on the result of combining the buffers to return to the time domain to produce a filtered signal, and outputting the filtered signal received from the processor.

In a particular case of this method, the combining all responses in each of said plurality of buffers may comprise: receiving a signal of interest; receiving a signal indicating that a stimulus has been applied; assigning each received signal associated with a stimulus to a plurality of buffers by: sampling the signal of interest at a time corresponding to the associated stimulus to obtain a sample signal; and assigning the sampled signal to one of the plurality of buffers in a biased manner based on a comparative statistic related to measure of presence or the ER signal.

In the above cases, the transform the combination of all responses in each buffer to a spectral domain may comprise performing a Discrete Wavelet Transform and the compare the spectral components of the buffers to determine a scaling factor may comprise determining the synchronicity as defined by the equation:

$$s_{n:r}(\tau) = \frac{\int_{\tau-\frac{T_n}{2}}^{\tau+\frac{T_n}{2}} A_{n:r}^{\Psi}(t) B_{n:r}^{\Psi}(t) dt}{\sqrt{\int_{\tau-\frac{T_n}{2}}^{\tau+\frac{T_n}{2}} (A_{n:r}^{\Psi}(t))^2 dt \cdot \int_{\tau-\frac{T_n}{2}}^{\tau+\frac{T_n}{2}} (B_{n:r}^{\Psi}(t))^2 dt}}$$

Where:
n represents the scale in the wavelet transform domain
r represents the value for a particular random ordering of the raw data
$\tau$ represents time relative to the start of the ER analysis window
$T_n$ represents the period of the wavelet transform for a particular scale n
$A^{\Psi}_{n:r}$ and $B^{\Psi}_{n:r}$ are the wavelet transforms of the A and B buffers.

BRIEF DESCRIPTION OF THE DRAWINGS

For a better understanding of the various embodiments described herein and to show more clearly how they may be carried into effect reference will now be made, by way of example only, to the accompanying drawings which show at least one exemplary embodiment and in which:

FIGS. 1A and 1B is an example diagram of the implementation of an adaptive filter that reduces or eliminates components of the transformed signal, such as the discrete wavelet transform, using an estimate of the noise spectrum based on acquired data. The method overcomes above-cited limitations of the methods of Causevic since no assumptions are made regarding the coherence of the spectrum of the signal relative to the spectrum of the noise and, in one embodiment (by excluding steps 1a and 1d), the method can be implemented without storing all raw data frames. Furthermore, the method can be implemented using a relatively efficient discrete wavelet transform algorithm.

FIG. 2 is an example of a method of buffering the data into subaverages to allow reliable estimation of synchronicity, overcoming the above-cited objections to conventional estimation of the noise spectrum from the difference between A and B buffers.

DETAILED DESCRIPTION

Figure 1B:
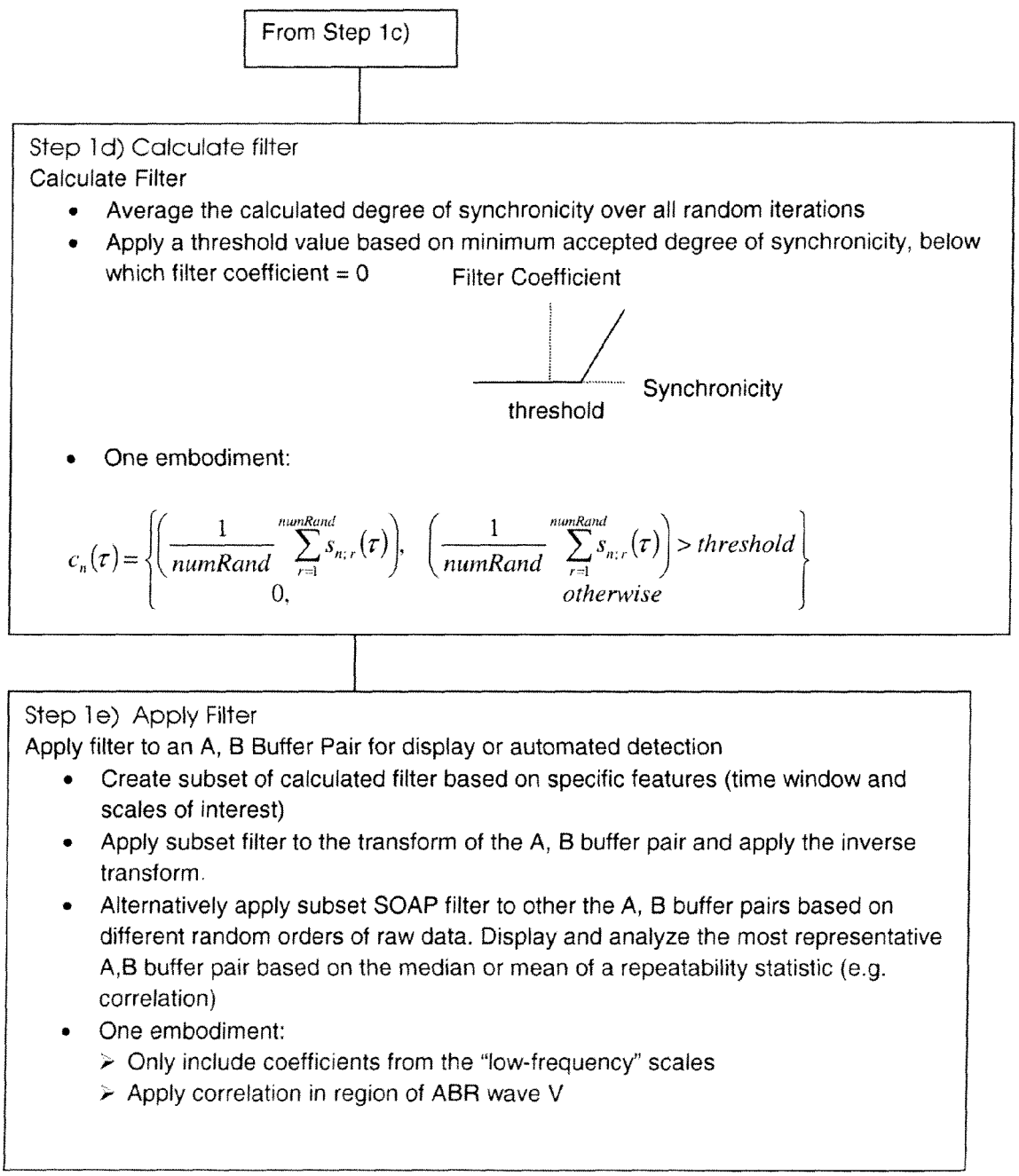
Figure 3:
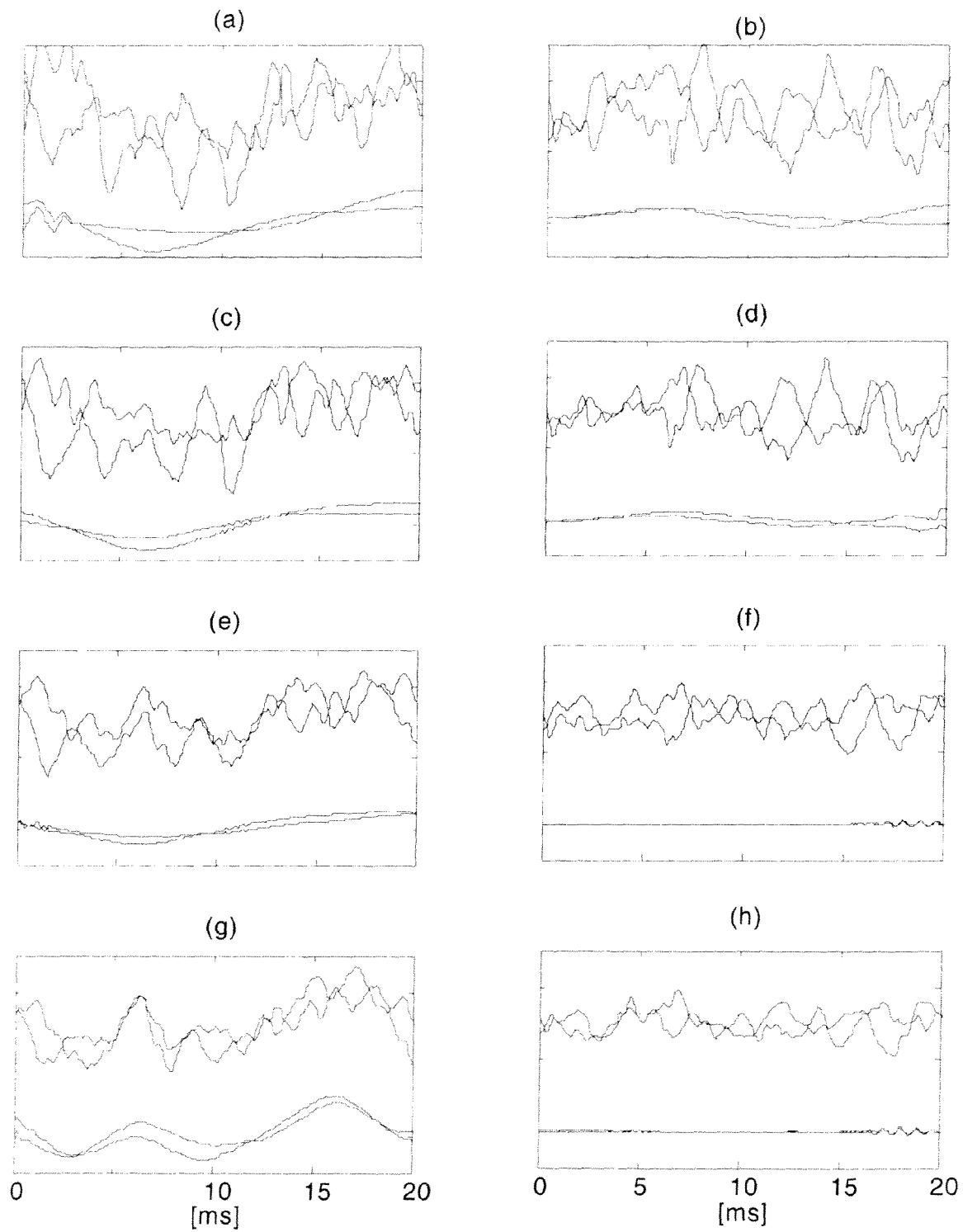
FIG. 3 compares the effect of the SOAP filter with Kalman weighted averaging techniques. The left column contain results when a 35 dB nHL click stimulus was presented and the right column when no stimulus was presented. Wave V is present around 7 ms post stimulus. The subject was moving continuously during the testing, including chewing gum and sucking candy. Each row presents data for 500, 1000, 2000, and 4000 stimuli in each buffer, respectively. Each subfigure contains two sets of waveforms: Kalman weighted average with random buffering (i.e. in the order of presentation) (top set) and the applied SOAP filter to the data (bottom set). Of note is the clear absence of a response in the SOAP filtered data in the no stimulus case. As well, in the stimulus present case, the SOAP filter results indicates a clear low frequency, which is possibly the 40 Hz cortical response. The SOAP filter was set up with a threshold of 0.5 and a desired percentile of 95 (increase percentile because more correlated signal Components are getting through the SOAP filter). The pre-SOAP filtered data was filtered with a second order Butterworth between 30 and 1500 Hz.
Figure 4:
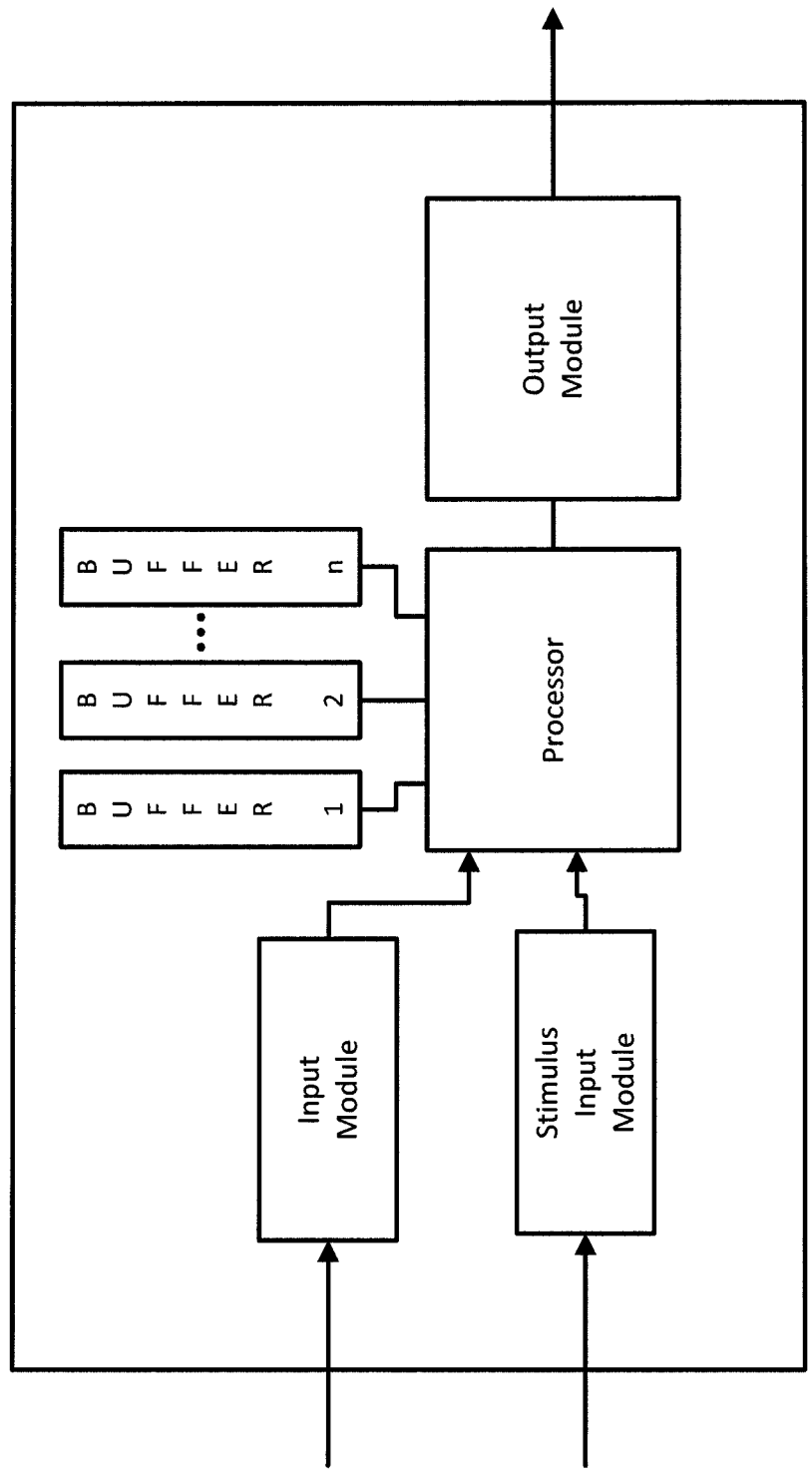
FIG. 4 shows a system for filtering a signal.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that some embodiments may be practiced without these specific details. In other instances, well-known methods, procedures and components have not been described in detail so as not to obscure the embodiments described herein. Further, the description is not to be considered as limiting the scope of the application and the claims herein.

General information on detecting signals in noise for various applications can be found in U.S. Pat. No. 6,778,955 to Xinde L I et al., which is hereby incorporated herein by reference.

Generally speaking, embodiments described herein relate to systems and methods for a new adaptive filtering technique intended to reduce the effect of noise on signals of interest generated from a stimulus. In a particular example, the adaptive filtering system and method is applied to EMG noise in ABR recordings. The technique involves adaptively estimating the spectrum of the noise in the recording and comparing it with the spectrum of the signal-plus-noise contained in the averaged response. Each spectral component is then rated according to its synchronicity based on a measure of synchronicity derived from the data collected. This technique makes use of the idea that, although the noise and signal of interest share the same transform space (i.e. overlapping frequency spectra in Fourier space and sharing the same scales and time in the discrete wavelet transform domain), the magnitudes of their individual spectral components are different.

A general embodiment is shown in FIGS. 1A and 1B. The system and process involve several components. An exemplary embodiment includes:

1) Receiving a signal generated by a transducer measuring a physiological signal, in particular one generated by a stimulus.

2) If necessary, conducting preprocessing on the signal.

3) Buffering the signal. One method of buffering the signal, which overcomes the limitations of conventional A and B buffering described above is summarized below and in FIG. 2.

4) Averaging of responses, in this case using weighted averaging (using Kalman-filter weighting based on the noise estimate obtained by calculating the variance of the signal in a single sweep).

5) performing a transform such as a Discrete Wavelet Transform or other wavelet transform.

6) determining synchronicity between the components of each buffer.

7) One measure of synchronicity, as noted, is the correlation between the transforms of the A and B buffers as a function of time and scale. The synchronicity may be calculated as follows:

$$s_{n:r}(\tau) = \frac{\int_{\tau-\frac{T_n}{2}}^{\tau+\frac{T_n}{2}} A_{n:r}^{\Psi}(t) B_{n:r}^{\Psi}(t) dt}{\sqrt{\int_{\tau-\frac{T_n}{2}}^{\tau+\frac{T_n}{2}} (A_{n:r}^{\Psi}(t))^2 dt \cdot \int_{\tau-\frac{T_n}{2}}^{\tau+\frac{T_n}{2}} (B_{n:r}^{\Psi}(t))^2 dt}}$$

Where:
n represents the scale in the wavelet transform domain
r represents the value for a particular random ordering of the raw data
$\tau$ represents time relative to the start of the ER analysis window
$T_n$ represents the period of the wavelet transform for a particular scale n
$A_{n:r}^{\Psi}$ and $B_{n:r}^{\Psi}$ are the wavelet transforms of the A and B buffers.

8) averaging the synchronicity function over the analysis time and all scales for several random orderings of the data 9) setting the wavelet components that are below a predetermined threshold for the synchronicity function (e.g. below 0) to 0. Setting other wavelet components to a value equal to or a function of the synchronicity function.

10) Transforming the buffered data (A, B, A+B, A−B) to be displayed to the user or to be analysed further using one or more automated detection algorithms. Applying the filter as per step 9) above. Applying the inverse transform to the data.

11) Optionally, applying step 10) above to different A and B buffers created with different random orderings of the data.

12) Selecting the A and B buffering for display and further analysis that is best, based on a repeatability measure such as correlation.

It will be understood that these components may be applied in a different order and that other embodiments are possible. For example, an alternative embodiment may alternately include:

1) applying the algorithm to a single random ordering of the data, 2) an alternate transform such as the Fourier Transform, 3) Straight averaging instead of weighted. Also there may be an artifact rejection threshold that's applied before averaging i.e., if the raw data is above the threshold that sweep is thrown out.

4) A different synchronicity function such as the ratio of variances of A+B and A−B.

5) In step 9) a threshold other than 0 may be used.

6) In step 11) the most representative buffering (with a median or mean correlation coefficient) may be used, rather than the best (i.e. the one with the highest correlation coefficient).

The current description also introduces a further noise and signal-to-noise estimation technique that improves on the buffering technique described above by assigning buffers in a biased manner, as represented in FIG. 2. The biasing is performed such that some measure/indicator of the presence or absence of the ER signal can be improved by the biasing of the buffer assignment. For example, in a particular case, the variance of the difference between the A and B buffers can be biased so that to be as close as possible to the statistically expected difference. Other measures of error or variation that compare the A and B buffers may alternatively be used and the buffer selection may be made to target the statistically expected value for the measure. In one embodiment, the statistically expected value may be the expected error predicted by the Kalman Filtering algorithm for weighted averaging (see J. eski, "New concept of signal averaging in time domain", Annual International Conference of the IEEE Engineering in Medicine and Biology Society, Vol. 13:1, 1991, 367-368). As an example, for each pair of single-sweep responses measured, the system calculates the coefficient for each possible permutation of buffer assignments so that the error measure remains as close as possible to the target throughout the test. It will be understood that other techniques will be available for assigning responses to buffers in a manner that biases the buffers, including, for example, assigning buffers based on permutations of the three most recent readings or the like. SCRUB processing reduces the variability in the spectrum of the noise estimate when compared with conventional random buffer assignment. The resulting coefficient of regression is a more reliable test statistic for distinguishing between the presence and absence of a response. Hence SCRUB™ processing avoids the disadvantages of interstimulus noise estimation by using the response data itself to obtain the estimate and it avoids the disadvantages of conventional buffering by reducing variability on the estimates of noise and ER signal.

A general embodiment is shown in FIG. 2. The system and process involve several components. An exemplary embodiment includes:

1) Collect 2 raw signal responses (Response1 and Response2) generated by a transducer measuring a physiological response, in particular a physiological signal generated by a 2 successive stimuli, at an input.

2) if necessary, conducting preprocessing on the signal at a preprocessing module.

4) Create two buffer pair candidates:

BufferingCandidate1) Response1 weighted and averaged to buffer A, Response2 to buffer B BufferingCandidate2) Response1 weighted and averaged to buffer B, Response2 to buffer A 5) Use Kalman weighted averaging to combine responses in buffer candidates 6) Compare the mean square error estimate generated by the Kalman-Filter weighting to the variance of the difference between buffers for the two buffer candidates.

7) Select the buffer candidate that minimizes the difference between the expected noise variance to the difference between the buffers for the two candidates i.e. minimizing the equation:

$$\left(E\{MSE\} - \sigma^2 \left(\frac{A1 - B2}{2}\right), E\{MSE\}\right)$$

8) Repeat from step 1.

It will be understood that these components/processes may be applied in a different order and that other embodiments are possible. For example, alternative embodiments may alternately include:

1) an alternate number of responses.

2) a different measure of noise, other than the variance of the difference in A and B buffers, such as the single point variance used in the $F_{SP}$ variance ratio discussed above.

3) A different method of predicting the expected value of the noise measure.

4) The selection of preferred buffering may be made according to a portion of the received response, e.g. the region where the evoked response is expected.

Those who are knowledgeable in the field will appreciate that there may be obvious variations and combinations of elements in the preceding systems and methods.

We claim:

1. A system for processing a noisy signal comprising multiple instances of a signal of interest added to noise, wherein each instance of the signal of interest is causally related to a stimulus, the system comprising:

an input module for receiving the noisy signal while a plurality of stimuli occur, each stimulus corresponding to a distinct instance of the signal of interest;

a plurality of memory buffers;

a processor configured to:

receive the noisy signal from the input module;

distribute a plurality of segments of the noisy signal, each segment corresponding to a stimulus, among at least two of the plurality of memory buffers;

within each of the at least two of the plurality of memory buffers, mathematically combine the plurality of segments to form a combined result for each of the at least two of the plurality of memory buffers;

transform the combined result for each of said plurality of memory buffers to a transform space to obtain transform components;

calculate a degree of synchronicity among select corresponding transform components for the plurality of memory buffers;

apply a scaling factor derived from the degree of synchronicity to select transform components; and apply an inverse transform to the scaled select transform components for the plurality of memory buffers to provide at least one filtered signal derived from the plurality of memory buffers, and an output module configured to output the at least one filtered signal, wherein each filtered signal represents the signal of interest.

2. The system of claim 1, wherein the processor is further configured to, prior to applying the scaling factor:

recursively, for a predetermined number of times:

randomly order the plurality of segments of the noisy signal among at least two of the plurality of memory buffers and combine the plurality of segments of the noisy signal within each of the at least two of the plurality of memory buffers to form a combined result for each of the at least two of the plurality of memory buffers;

transform the combined result for each of said plurality of memory buffers to a transform space to obtain transform components; and calculate a degree of synchronicity among select corresponding transform components for the plurality of memory buffers, derive a final degree of synchronicity from among the degrees of synchronicity for each random ordering; and utilize the final degree of synchronicity as the scaling factor when applying the scaling factor to select transform components.

3. The system of claim 2, wherein the processor is further configured to distribute the plurality of segments of the noisy signal among at least two of the plurality of memory buffers by:

assigning the plurality of segments of the noisy signal to the plurality of memory buffers in a biased manner so that the reliability of a comparative statistic is increased.

4. The system of claim 1, wherein the processor is further configured to distribute the plurality of segments of the noisy signal among at least two of the plurality of memory buffers by:

assigning the plurality of segments of the noisy signal to the plurality of memory buffers in a biased manner so that the reliability of a comparative statistic is increased.

5. The system of claim 1, wherein the stimulus is a recurring feature of a steady state waveform.

6. The system of claim 5, wherein the steady state waveform is an auditory steady state signal and the recurring feature is a fixed phase of the auditory steady state signal.

7. The system of claim 1, wherein the stimulus is a sensory stimulus and the signal of interest is a physiological response.

8. The system of claim 7, wherein the sensory stimulus is an auditory stimulus.

9. The system of claim 1, wherein the processor is configured to perform the transform on each of the plurality of segments before combining the plurality of segments within each of said plurality of memory buffers.

10. The system of claim 1, wherein the scaling factor further comprises a predetermined threshold.

11. The system of claim 1, wherein the processor is further configured to, after calculating a degree of synchronicity, determine a presence of at least two instances of the signal of interest based on a value of the degree of synchronicity for at least one of the transform components.

12. The system of claim 11, wherein the processor is configured to determine the presence of the signal of interest based on at least one of the degrees of synchronicity satisfying a predetermined threshold.

13. A system for buffering a noisy signal comprising multiple instances of a signal of interest added to noise, wherein each instance of the signal of interest is causally related to a stimulus, the system comprising:
an input module for receiving the noisy signal while a plurality of stimuli occur, each stimulus corresponding to a distinct instance of the signal of interest;
a plurality of memory buffers;
a processor configured to:
receive the noisy signal from the input module;
assign a plurality of segments of the noisy signal, each segment corresponding to a stimulus, to the plurality of memory buffers in a biased manner so that the reliability of a comparative statistic is increased; and
an output module configured to output the contents of at least one of the plurality of memory buffers or a value of the comparative statistic for further processing.

14. The system of claim 13, wherein the processor is further configured to determine a presence of at least two instances of the signal of interest based on the comparative statistic.

15. The system of claim 14, wherein the processor is configured to determine the presence of at least two instances of the signal of interest based on the comparative statistic satisfying a predetermined threshold.

16. A system for buffering a noisy signal comprising multiple instances of a signal of interest added to noise, wherein each instance of the signal of interest is causally related to a stimulus, the system comprising:
an input module for receiving the noisy signal while a plurality of stimuli occur, each stimulus corresponding to a distinct instance of the signal of interest;
a plurality of memory buffers;
a processor configured to:
receive the noisy signal from the input module;
recursively, for a predetermined number of times:
randomly order a plurality of segments of the noisy signal and assign the plurality of segments of the noisy signal to the plurality of memory buffers in a random manner;
calculate a comparative statistic for each random ordering;
select a random ordering having a final comparative statistic that is representative of a distribution of the comparative statistics
an output module configured to output the selected random ordering for further processing.

17. The system of claim 16, wherein the processor is further configured to determine a presence of the signal of interest based on the comparative statistic.

18. The system of claim 17, wherein the processor is configured to determine the presence of the signal of interest based on the comparative statistic satisfying a predetermined threshold.

* * * * *